United States Patent [19]

Kamstra

[11] Patent Number: 4,573,971
[45] Date of Patent: Mar. 4, 1986

[54] AUTOMATIC INJECTION DEVICE

[75] Inventor: Paulus R. Kamstra, Olst, Netherlands

[73] Assignee: Duphar International Research B.V., Weesp, Netherlands

[21] Appl. No.: 560,925

[22] Filed: Dec. 13, 1983

Related U.S. Application Data

[63] Continuation-in-part of Ser. No. 405,367, Aug. 5, 1982, Pat. No. 4,529,403.

[30] Foreign Application Priority Data

Aug. 10, 1981 [NL] Netherlands ......................... 8103744

[51] Int. Cl.⁴ .............................................. A61M 5/00
[52] U.S. Cl. ................................................... 604/191
[58] Field of Search ............... 604/191, 232, 134, 135, 604/139, 239, 89, 90, 91, 203, 238; 206/528, 538

[56] References Cited

U.S. PATENT DOCUMENTS

| | | | |
|---|---|---|---|
| 2,591,046 | 4/1952 | Brown | 604/82 |
| 2,717,601 | 9/1955 | Brown . | |
| 3,330,282 | 7/1967 | Visser et al. . | |
| 3,881,484 | 5/1975 | Gidcumb, Jr. | 604/191 |
| 3,914,419 | 10/1975 | Haeger et al. . | |
| 4,031,893 | 6/1977 | Kaplan et al. | 604/136 |
| 4,226,235 | 10/1980 | Sarnoff et al. . | |
| 4,235,235 | 11/1980 | Bekkering | 604/238 |
| 4,394,863 | 7/1983 | Bartner | 604/191 |

FOREIGN PATENT DOCUMENTS

| | | |
|---|---|---|
| 2110516 | of 1972 | France . |
| 871854 | 7/1961 | United Kingdom . |
| 1318803 | 5/1973 | United Kingdom . |
| 1449986 | 9/1976 | United Kingdom . |
| 2010681 | 7/1979 | United Kingdom . |

Primary Examiner—C. Fred Rosenbaum
Assistant Examiner—Christa K. Scott
Attorney, Agent, or Firm—Stevens, Davis, Miller & Mosher

[57] ABSTRACT

An automatic device for injecting two or more different injection liquids which may not be in contact with each other for long periods of time, and including a combination of a discharge mechanism, a cartridge holder and a cartridge slidably accommodated in the holder and including an ampoule, a piston movable in the ampoule for sealing same, and a hypodermic needle connected to the front of the ampoule by a needle mount.

12 Claims, 5 Drawing Figures

AUTOMATIC INJECTION DEVICE

Continuation-in-part of U.S. patent application Ser. No. 405,367 filed Aug. 5, 1982 and now U.S. Pat. No. 4,529,403.

The invention relates to an automatic device for injecting two or more different injection liquids which may not be in contact with each other for longer periods of time, a so-called "plural injection device."

In an automatic injector, an ampoule and a hypodermic needle in operative association therewith is driven by the force of a power source so as to insert the needle and then to inject the injection liquid present in the ampoule. Such an injector comprises a combination of a discharge mechanism, a cartridge holder and a cartridge which is slidably accomodated in the cartridge holder and which comprises an ampoule, a piston which is movable in the ampoule and seals same, and a hypodermic needle which is connected to the front of the ampoule and, if desired, is covered by a flexible sheath to maintain the needle in a sterile condition. The discharge mechanism is provided with a power source which can move the cartridge from an inoperative condition to an operative condition. The injector furthermore comprises locking means to control the actuation of the power source and preferably a safety device to block said locking means.

Automatic injectors have been developed especially for use by persons who have to administer an injection into their own body at an instant which is not known beforehand. These persons include, for example, persons having an increased risk of a cardial infarct or soldiers after having been exposed to an enemy's battle gas, for example, a nerve gas. It will therefore be obvious that high requirements have to be imposed upon automatic injectors as regards the reliability and the handlability. Such injectors are usually stored for years at a stretch and in addition are carried with the potential user under varying conditions for a long period of time; the operation of the injector must be sufficiently ensured at the critical instant. When said critical moment has come, it must be possible to handle the injector rapidly and easily and to be used efficaciously.

It may be desired, however, to be able to inject several medicaments at that instant which are not compatible during the storage time. In particular for military applications, the administration of several medicaments or antidotes is often necessary, for instance to reach an effective therapy, or because it is not known beforehand which battle gas as to nature and composition will be used by the enemy. Said medicaments are often not compatible with each other during the long storage time of the injector.

It is not advisable to use several automatic injectors filled with different injection liquids in the above-described emergency situation: There is a fair chance that a mistake is made in choosing the correct injectors, it would last too long before all the desired medicaments would have been injected, and it is objectionable for a person to carry several injectors with him for a long period of time. Therefore, one single device is desired in which more different injection liquids which may not be in contact with each other for a longer period of time can be stored while separated from each other, but with which, if necessary, the injection liquids can be injected simultaneously or substantially simultaneously.

Such a device is known from U.S. Pat. No. 3,572,336. Injection liquids which are poorly compatible or are not at all compatible with each other can be injected simultaneously by means of the device described and shown in said Patent Specification. For that purpose, a number of medicament holders are in operative association with a number of needles or with one needle via a mixing chamber. A piston is present in each medicament holder, while the collective pistons are connected through separate piston rods to one common piston rod so that under the influence of a coiled spring the medicament holders can simultaneously be emptied. The injector known from the above-mentioned United States Patent is very complicated and hence less reliable than would be desired. In fact, the possibility of a component not operating satisfactorily, as a result of which the injector would fail at the critical moment, is the larger according as the device comprises more components which are to give the desired result in cooperation with each other. In addition, the cost-price of such a complicated device will be high, as a result of which one may be inclined to replace the device less rapidly than is desirable; as a result of this the reliability of the system is also adversely influenced.

Another "plural injecting device" is known from European Patent Application No. 14006. The device described in said Application consists of a number of separate automatic single-compartment injectors which are together assembled in one outer casing in such manner that upon activation of one of the injectors the other ones also become operative so that all injection liquids are simultaneously injected. This device is destined in particular for military application. The composition of enemy's battle gases varies regularly so that it is desired to replace from time to time in stored automatic injectors an antidote which is active against a given battle gas component. This can be done particularly easily in the "plural injecting device" known from the last-mentioned Patent Application, namely by simply exchanging one of the single-compartment injectors therein by one having a different antidote. However, the disadvantage of the "plural injecting device" described in the above-mentioned Patent Application is the bulkiness and the weight, as a result of which said device is less easy to carry and to use in case of need. It is the object of the invention to provide an automatic device for injecting two or more different injection liquids which may not be in contact with each other for a longer period of time, which device must satisfy the following conditions: (1) easy handlability, (2) reliability, and (3) simplicity of construction so that the cost of manufacture can be kept low.

This object can be achieved by means of an automatic injector, comprising a combination of a discharge mechanism, a cartridge holder and a cartridge which is slidably accomodated in the cartridge holder and which comprises an ampoule, a piston which is movable in the ampoule and seals same, and a hypodermic needle which is connected to the front of the ampoule by means of a needle mount, and, if desired, is covered by a flexible sheath to maintain the needle in a sterile condition, which device according to the invention is characterized in (1) that the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, (2) that the needle mount comprises a collar connected to the front of the ampoule and a neck in which the injection needle is sealingly connected, (3) that the rear face of the neck of the needle mount or the front face of the stopper nearest to the rear face of the neck of the needle mount comprises a few spacing supports, and (4) that the inner wall of the ampoule is locally deformed between the needle mount and the stopper or foremost stopper over a length which is slightly larger than the length of the stopper or the collected stoppers in such a manner that upon actuation of the device a by-pass is formed allowing the injection liquid or liquids behind the stopper or stoppers to reach the cannula past the stopper or stoppers.

A very important additional advantage of the device according to the invention is the flexibility of the liquid compartments. In the known injectors the contents of the liquid compartments are determined by the dimensions of the medicament holders, while the number of liquid compartments is entirely fixed once a given construction has been chosen. On the other hand, the contents of the liquid compartments of the device according to the invention is fully variable because the distance between the piston and the stopper, between the stopper and the needle connection, and, if more stoppers are present, between the stoppers mutually can be adjusted at will. The number of liquid compartments can also be chosen at will by varying the number of stoppers in the ampoule between piston and needle mount; only the length of the by-pass means for the injection liquid or liquids must be adapted to the overall length of the collective stoppers.

In a preferred embodiment of the automatic injection device of the invention the ampoule and the needle mount are integrally formed from a rigid synthetic material, while the local deformation of the inner wall of the ampoule comprises one or more ridges which extend in the longitudinal direction of the ampoule over a length which is slightly larger than the length of the stopper or the collected stoppers. In said embodiment preferably the rear face of the neck of the needle mount comprises as spacing supports one or more ridges which are formed as an extension of the ridge or ridges on the inner wall of the ampoule.

The following demands should be made upon the synthetic material, from which the ampoule and the needle mount are manufactured: impermeable for the injection liquids, sufficiently vapour-tight and compatible with the medicaments.

In another equally preferred embodiment the automatic injection device of the invention is constructed in such manner that an annular member of resilient material is provided in the front of the ampoule for sealing the connection between the front of the ampoule and the collar of the needle mount, and that the inner wall of the ampoule is locally deformed between the rear face of the annular member and the stopper or foremost stopper. Said annular member provides a reliable vapour-tight sealing between the front of the ampoule and the collar of the needle mount. The ampoule may be manufactured from glass or from a suitable synthetic material with the requirements as described for the previous embodiment.

The local deformation of the inner wall of the ampoule to provide a by-pass for the injection liquid or liquids may be in the form of one or more ridges as described for the previous embodiment or of one or more slots recessed in said inner wall. Preferably, however, the wall of the ampoule is locally deformed so as to present one or more bulges, the length of which is slightly larger than the length of the stopper or the collected stoppers. To allow the injection liquids to reach the cannula preferably the front face of the stopper nearest to the rear face of the neck of the needle mount comprises a few spacing supports. Alternatively, the rear face of the neck of the needle mount or of the annular member may comprise said spacing supports. The spacing supports may be three or more projections, for example in the form of caps or truncated cones. The needle mount is manufactured from a form-retaining synthetic material by a moulding process. The foremost injection liquid is preferably present between the foremost stopper on the one hand and the needle mount and/or the annular member on the other. If this injection liquid is in contact with the needle mount the material of the needle mount should be impermeable for the foremost injection liquid, sufficiently vapour-tight and compatible with the medicament in said injection liquid.

BRIEF DESCRIPTION OF THE DRAWINGS

The invention will now be described in greater detail with reference to preferred embodiments which are shown in the drawings, in which.

DESCRIPTION OF THE PREFERRED EMBODIMENTS

Figure 1:
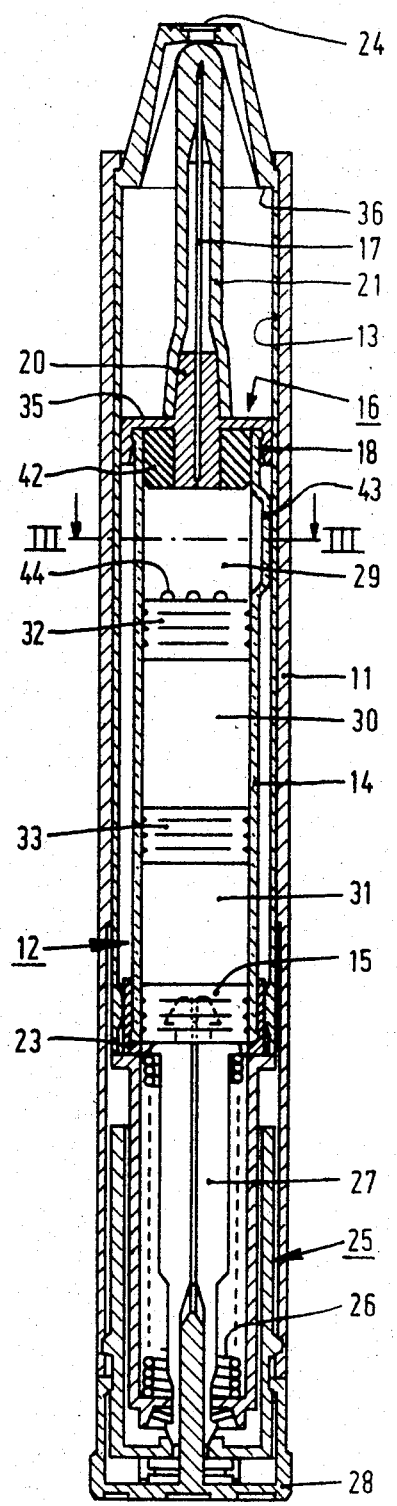
FIG. 1 is a longitudinal sectional view of an injection device according to the invention in the condition in which it can be transported and stored.
Figure 3:
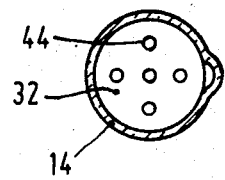
FIG. 3 is a cross-sectional view through the ampoule of the device of FIG. 1, viz. taken on the line III—III of FIG. 1, viewed in the direction of the stopper.

The injection device shown in FIGS. 1 and 3 is constructed for the greater part as described in detail and shown in Netherlands Patent Specification No. 160.725 in the name of Applicants. In broad outline the device comprises a cylindrical outer sleeve 11 in which a cartridge assembly 12 is provided so as to be slidable, comprising a cartridge holder sleeve or inner sleeve 13 fitting in the outer sleeve, a cylindrical glass ampoule 14 containing injection liquids, a piston 15 at one end and a needle mount 16 with injection needle 17 at the other end of the ampoule. At each end the ampoule comprises a radially outwardly projecting flange around which on the side of the injection needle the needle mount is connected by means of a collar 18. The needle mount furthermore comprises a neck 20 in which the needle 17 having a flexible needle guard 21 is connected. An annular member 42 is provided between the front of the ampoule and a rearward extension of the neck 20 of the needle mount, in thus manner that a vapour-tight sealing between ampoule and needle mount is obtained. The annular member as well as the piston 15 and the stoppers (32, 33—see further) are manufactured from a flexible material, preferably rubber of a pharmaceutical quality. An externally cylindrical sliding sleeve 23 which is slidable in the cartridge holder sleeve 13 is connected around the flange at the other end of the ampoule. The cartridge assembly 12 is provided in the outer sleeve 11 in such manner that the closed end of the needle guard 21 bears against the end of the cartridge holder sleeve 13 having a bore 24. The outer sleeve 11 has such a length that the cartridge assembly 12 is accommodated in one end and the discharge mechanism 25 is accommodated in the other end. The discharge mechanism which comprises a coil spring 26 as a power source is exactly equal to the spring power assembly described in the above-mentioned Netherlands Patent Specification No. 160,725, and comprises locking means 27 and a safety device 28.

Internally the ampoule 14 is divided into three separated liquid compartments 29, 30 and 31 by means of two cylindrical stoppers 32 and 33 which, like the piston, have a slightly larger diameter than the inside diameter of the ampoule.

Close behind the rear face of the annular member 42 the wall of the ampoule is deformed so as to present a bulge 43 extending in the longitudinal direction of the ampoule. The bulge in the ampoule wall is slightly longer than the two stoppers collectively, so that the end of the bulge remote from the needle mount has just become uncovered when the stoppers have been moved forward entirely to against the rear face of the annular member.

The front face of the front stopper 32 comprises spacing supports 44, for example, in the form of five caps or truncated cones.

When the injection device shown in FIGS. 1 and 3 is actuated, the cartridge assembly moves forward under the influence of the spring, the sliding sleeve 23 moving in the cartridge holder sleeve. The needle guard is compressed, the needle perforating the closed end of the needle guard and entering into the body in that place where the injection is to be administered. When the needle is in its foremost position, in which the needle mount is stopped in that the front 35 of the collar of the needle mount abuts against a shoulder 36 formed by a constriction in the cartridge holder neck, the forward movement of the piston begins under the influence of the same spring, so that a beginning of the actual injection is made. The injection liquid in compartment 29 is now injected, the whole assembly of piston 15, stoppers 32 and 33 and liquid columns 30 and 31 moving forward. When the stopper 32 has moved in the ampoule over such a distance that the rear of said stopper has passed the rearward end of the bulge 43, the injection liquid in compartment 30 can reach the cannula through the by-pass. When all the injection liquid from the compartments 29 and 30 has been injected, the spacing supports on the front face of stopper 32 are present just against the rear face of the annular member and stoppers 32 and 33 bear against each other. At that instant stopper 33 has moved forward over such a distance that the rear face of said stopper leaves the rearward end of the bulge 43 just uncovered so that the injection liquid in compartment 31 can also reach the cannula and can be injected.

Figure 2:
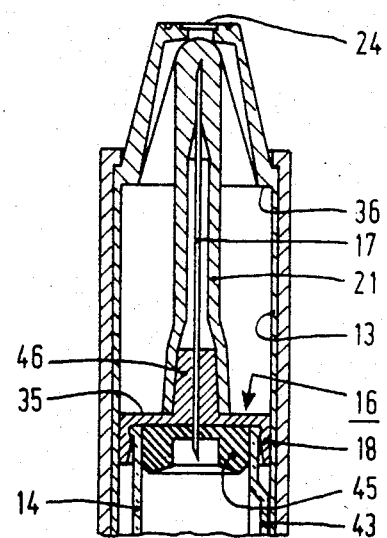
FIG. 2 is a slightly different embodiment of the frontside of the cartridge assembly of the device as shown in FIG. 1.

In another embodiment of the cartridge assembly for the injection device of the inventions the front side of which is shown in FIG. 2, the neck 46 of the needle mount is not provided with a rearward extension, while the annular member 45 sealingly encloses the rearward end of the injection needle 17. This embodiment is especially suitable when a glass ampoule is used and the foremost injection liquid is not allowed to be in contact with the material of the needle mount during storage of the device.

Figure 4:
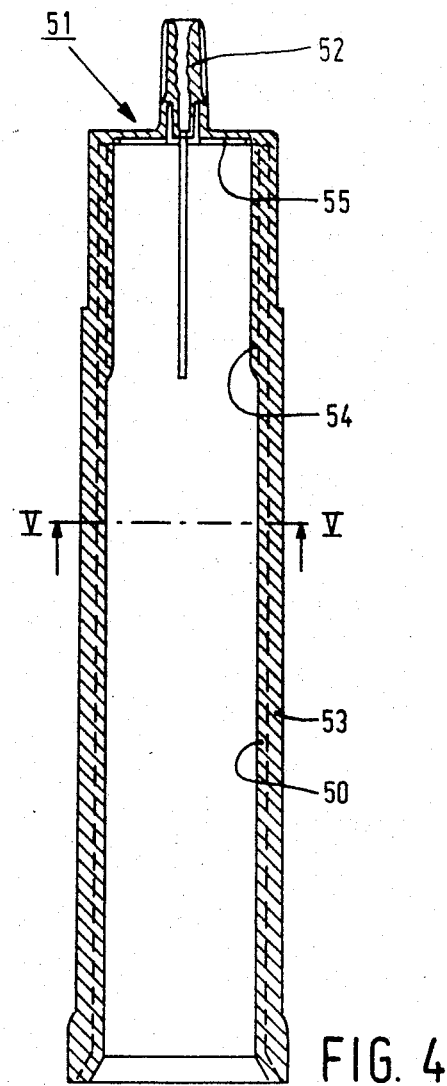
FIG. 4 shows a different embodiment of an ampoule plus needle mount of an injection device according to the invention, in longitudinal sectional view.
Figure 5:
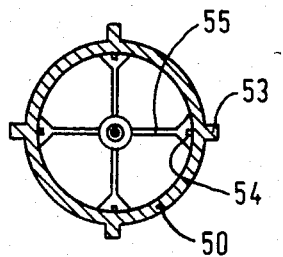
FIG. 5 is a cross-sectional view through the ampoule of FIG. 4, viz. taken on the line V—V of FIG. 4, viewed in the direction of the needle mount.

In another embodiment of the injection device of the invention, only the essential parts of which are presented in FIGS. 4 and 5, the ampoule 50 and the needle mount 51 are integrally manufactured from a rigid synthetic material, preferably a polyolefin, e.g. polypropylene, by a moulding process. The neck 52 of the needle mount form a connection means for the injection needle. The ampoule is outwardly provided with four strengthening ribs 53 having a smaller outside diameter towards the needle connection and a larger one towards the rearward end of the ampoule. These ribs also serve for a good centring of the ampoule in the cartridge holder sleeve 13 (FIG. 1) of the injection device. Nearby the needle connection the inner wall of the ampoule is provided with four ridges 54, extending in the longitudinal direction and having an approximately rectangular cross-section. The rear face of the neck of the needle mount also comprises four ridges 55 as extensions of and integrally formed with ridges 54. Two stoppers (not shown in FIG. 4) can be used in the ampoule 50 for dividing the ampoule into three separated liquid compartments, viz. between the piston in the rearward end of the ampoule and the rearmost stopper, between the two stoppers, and between the foremost stopper and the rear face of the neck of the needle mount. The ridges 54 on the inner wall of the ampoule are slightly longer than the two stoppers collectively, so that the ends of the ridges remote from the needle connection have just become uncovered when the stoppers have been moved forward entirely to against the ridges 55 on the rear face of the neck of the needle mount. When the injection device comprising the ampoule plus needle mount shown in FIG. 4 is used, the stoppers are moved forward and are deformed during passage of the ridges 54, small ducts being formed on either side of each ridge.

I claim:
1. An automatic device for injecting two or more different injection liquids which may not be in contact with each other for long periods of time, comprising a combination of a discharge mechanism, a cartridge holder and a cartridge which is slidably accommodated in the holder and which comprises an ampoule, a piston which is movable in the ampoule and seals same, and a hypodermic needle connected to the front of the ampoule by means of a needle mount, and, if desired, covered by a flexible sheath to maintain the needle in a sterile condition, said device being characterized in (a) that said cartridge includes said injection liquids and the ampoule between the piston and the needle mount comprises one or more stoppers which are movable in the ampoule and which, before use of the device, keep the injection liquids present in the ampoule separated from each other in that their circumference adjoins the inner wall of the ampoule in a sealing manner, (b) that said cartridge includes means maintaining most of the peripheral area of said ampoule in radially spaced relationship from said holder, (c) that the needle mount comprises a neck connected to the front of said ampoule in which the injection needle is sealingly connected, (d) that the rear face of the neck of the needle mount or the front face of the stopper nearest to the rear face of the neck of the needle mount comprises a plurality of spacing supports, and (e) that the inner wall of the ampoule is locally deformed between the needle mount and the stopper or foremost stopper over a length which is slightly larger than the length of the stopper or the collected stoppers in such a manner that upon actuation of the device a bypass is formed, allowing the injection liquid or liquids behind the stopper or stoppers to reach the needle past the stopper or stoppers.

2. A device as claimed in claim 1, characterized in that the ampoule and the needle mount are integrally formed from a rigid synthetic material and that the local deformation of the inner wall of the ampoule comprises one or more radially inwardly directed ridges which extend in the longitudinal direction of the ampoule over a length which is slightly larger than the length of the stopper or the collected stoppers.

3. A device as claimed in claim 2, characterized in that the rear face of the neck of the needle mount comprises as said spacing supports one or more ridges which are formed as an extension of the ridge or ridges on the inner wall of the ampoule.

4. A device as claimed in claim 3, characterized in that an annular member of resilient material is provided in the front of the ampoule for sealing the connection between the front of the ampoule and the collar of the needle mount, and that the inner wall of the ampoule is locally deformed between the rear face of the annular member and the stopper or foremost stopper.

5. A device as claimed in claim 4, characterized in that the wall of the ampoule is locally deformed so as to present one or more bulges, the length of which is slightly larger than the length of the stopper or the collected stoppers.

6. A device as claimed in claim 1, wherein said means maintaining said ampoule in spaced relationship from said holder comprises a collar connected to the front of said ampoule and which, together with said neck, constitutes said needle mount.

7. A device as claimed in claim 1, wherein said means maintaining said ampoule in spaced relationship from said holder comprises a plurality of radially outwardly directed ribs provided on the outer surface of said ampoule.

8. A device as claimed in claim 7, characterized in that the ampoule and the needle mount are integrally formed from a rigid synthetic material and that the local deformation of the inner wall of the ampoule comprises one or more radially inwardly directed ridges which extend in the longitudinal direction of the ampoule over a length which is slightly larger than the length of the stopper or the collected stoppers.

9. A device as claimed in claim 8, characterized in that the rear face of the neck of the needle mount comprises as said spacing supports one or more ridges which are formed as an extension of the ridge or ridges on the inner wall of the ampoule.

10. A device as claimed in claim 1, wherein the inner surface of said holder is substantially cylindrical over substantially the entire length traveled by said cartridge upon actuation of said device.

11. A device as claimed in claim 6, wherein the inner surface of said holder is substantially cylindrical over substantially the entire length traveled by said cartridge upon actuation of said device.

12. A device as claimed in claim 7, wherein the inner surface of said holder is substantially cylindrical over substantially the entire length traveled by said cartridge upon actuation of said device.

* * * * *